(12) United States Patent
Stojan

(10) Patent No.: US 8,637,096 B2
(45) Date of Patent: Jan. 28, 2014

(54) COMPOSITIONS AND METHOD FOR ENHANCING INSULIN ACTIVITY

(76) Inventor: Curtis C. Stojan, Huntley, IL (US)

( * ) Notice: Subject to any disclaimer, the term of this patent is extended or adjusted under 35 U.S.C. 154(b) by 56 days.

(21) Appl. No.: 13/524,485

(22) Filed: Jun. 15, 2012

(65) Prior Publication Data

US 2012/0269911 A1    Oct. 25, 2012

Related U.S. Application Data

(63) Continuation-in-part of application No. 12/959,868, filed on Dec. 3, 2010, now abandoned.

(60) Provisional application No. 61/283,498, filed on Dec. 4, 2009.

(51) Int. Cl.

| A61K 36/45 | (2006.01) |
|---|---|
| A61K 36/906 | (2006.01) |
| A61K 36/736 | (2006.01) |
| A61K 36/82 | (2006.01) |
| A61K 36/886 | (2006.01) |
| A61K 36/02 | (2006.01) |

(52) U.S. Cl.
USPC ...... 424/732; 424/195.17; 424/756; 424/735; 424/729; 424/744

(58) Field of Classification Search
None
See application file for complete search history.

(56) References Cited

U.S. PATENT DOCUMENTS

| 4,472,376 A | 9/1984 | Kamishita |
|---|---|---|
| 4,871,542 A | 10/1989 | Vilhardt |
| 5,618,913 A | 4/1997 | Brange |
| 5,681,580 A | 10/1997 | Jang |
| 5,866,538 A | 2/1999 | Norup |
| 6,399,566 B1 | 6/2002 | Dardai |
| 6,683,080 B2 | 1/2004 | Fryburg |
| 6,969,725 B2 | 11/2005 | Binggeli |
| 7,033,998 B2 | 4/2006 | Fishman |
| 2002/0151467 A1 | 10/2002 | Leung |
| 2004/0033954 A1 | 2/2004 | Sleeman |
| 2004/0204500 A1 | 10/2004 | Sugiyama |
| 2006/0094682 A1 | 5/2006 | Westwick |
| 2006/0147539 A1 | 7/2006 | Sung |
| 2006/0286182 A1 | 12/2006 | Patel |
| 2007/0015826 A1 | 1/2007 | Sreejayan |

*Primary Examiner* — Chris R Tate
*Assistant Examiner* — Russell Fiebig
(74) *Attorney, Agent, or Firm* — J. Wiley Horton; Adrienne C. Love

(57) ABSTRACT

A new treatment for individuals suffering from type 2 diabetes. The formulation used in the treatment includes a mixture of a thiazoleineione, an insulin, cinnamon bark extract, and at least one synergistic supplement selected from the group consisting of blueberry leaf extract, cranberry extract, kelp extract, sugar sea beet extract, acerola berry extract; ginger root extract, black cherry extract, green tea extract, Irish moss extract, *aloe vera* extract, and Stevia leaf extract. The thiazoleineione is preferably pioglitazone. The insulin is preferably an Insulin Aspart of rDNA origin. It is preferred that the cinnamon bark extract and synergistic supplement be in the form of a liquid concentrate.

10 Claims, No Drawings

US 8,637,096 B2

COMPOSITIONS AND METHOD FOR ENHANCING INSULIN ACTIVITY

CROSS-REFERENCES TO RELATED APPLICATIONS

This non-provisional application is a continuation-in-part of U.S. patent application Ser. No. 12/959,868 (filed Dec. 3, 2010 now abandoned). The continuation-in-part application lists the same inventor and an additional inventor.

This application claims the benefit, under 37 C.F.R. §119 of an earlier-filed provisional application. The provisional application was filed on Dec. 4, 2009. Dec. 4, 2010 falls on a Saturday. The prior application was assigned Ser. No. 61/283,498. It named the same inventor.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to pharmaceutical compositions that are useful for prevention and treatment of metabolic disorders, including insulin resistance syndromes, type 2 diabetes, weight gain, and cardiovascular disease. More specifically, the invention comprises compositions and therapeutic methods utilizing such compositions to increase insulin sensitivity.

2. Description of the Related Art

Type 2 diabetes is the most common form of diabetes, affecting many people worldwide. The disease is characterized by impaired insulin secretion and tissue insulin resistance. Insulin is produced by the Islets of Langerhans in the pancreas and regulates carbohydrate metabolism. Apart from its role in regulating carbohydrate homeostasis, insulin affects fat metabolism and liver activity. In particular, insulin affects the liver's activity in storing and releasing glucose and in processing blood lipids. Metabolic syndromes characterized by insulin resistance are usually associated with other cardiovascular risk factors including obesity, elevated plasma triglycerides, elevated plasma fibrinogen and plasminogen activator inhibitor-1, and elevated blood pressure.

Various therapies are prescribed for treatment and prevention of type 2 diabetes mellitus. The efficacy of each current therapy varies from one patient to another. Thiazoleineiones (TZD's) are one group of compounds used in the treatment of type 2 diabetes. TZD's are typically consumed orally and act as a ligand for the peroxisome proliferator-activated receptor gamma (PPARγ) located in the nucleus of adipocytes. TZD's are known for their ability to decrease insulin resistance. Examples of commercially available FDA-approved TZD's include rosiglitazone (Avandia from GlaxoSmithKline) and pioglitazone (Actos from Takeda Pharmaceuticals Company).

PPARγ agonist treatment of type 2 diabetes has many beneficial affects, including: reduced glucose levels; increased insulin sensitivity and improved β-cell function; increased HDL levels; lowered diastolic blood pressure and increased levels of the fibrinolytic plasminogen activator inhibitor-1 (PAI-1) [Zinman B. PPAR gamma agonists in type 2 diabetes: how far have we come in 'preventing the inevitable'? A review of the metabolic effects of rosiglitazone. Diabetes Obes Metab. August 2001; 3 Suppl 1:S34-43].

Despite these beneficial affects of TZD-based therapy, many patients are either completely nonresponsive to TZD's or must supplement the therapy with insulin or insulintropic drugs. Furthermore, TZD's are known to have adverse side effects which include weight gain, edema, upper respiratory tract infection and headache [Larsen T M, Toubro S, Astrup A. PPARgamma agonists in the treatment of type II diabetes: is increased fatness commensurate with long-term efficacy? Int J Obes Relat Metab Disord. February 2003; 27(2):147-161]. As such, there remains a need for therapies which would increase the percentage of patients responding to TZD's and/or decrease the side effects associated with the use of TZD's. The present invention proposes a composition and related therapy which achieves these goals.

Furthermore, the prior art in the field of diabetes treatment has been dominated by injected formulations. Specifically, the prior art is composed mainly of low-viscosity formulations intended to be injected subcutaneously. The risks associated with this approach are manifold and well known. They include repetitive injection injuries and infections.

BRIEF SUMMARY OF THE INVENTION

The present invention comprises a new treatment for individuals suffering from type 1 and type 2 diabetes. The formulation used in the treatment includes a mixture of a thiazoleineione, an insulin, cinnamon bark extract, and at least one synergistic supplement selected from the group consisting of blueberry leaf extract, cranberry extract, kelp extract, sugar sea beet extract, acerola berry extract, ginger root extract, black cherry extract, green tea extract, Irish moss extract, *aloe vera* extract, and Stevia leaf extract. The thiazoleineione is preferably pioglitazone. The insulin is preferably an Insulin Aspart of rDNA origin (such as NovoLog by Norvo Nordisk). It is preferred that the cinnamon bark extract and synergistic supplement be in the form of a liquid concentrate (such as Cinnergen by Nutra Lab).

One particularly effective formulation includes 1 part Insulin Aspart, 1 part pioglitazone, and 2 parts Cinnergen by volume. The formulation is preferably administered in 30 cubic centimeter dosages 3 times a day. The formulation is particularly effective when administered through the urethra.

DETAILED DESCRIPTION OF THE INVENTION

The present invention comprises a new treatment for individuals suffering from type 1 and type 2 diabetes. The formulation used in the treatment includes a mixture of a thiazoleineione, an insulin, cinnamon bark extract, and at least one synergistic supplement selected from the group consisting of blueberry leaf extract, cranberry extract, kelp extract, sugar sea beet extract, acerola berry extract, ginger root extract, black cherry extract, green tea extract, Irish moss extract, *aloe vera* extract, and Stevia leaf extract. The thiazoleineione is preferably pioglitazone hydrochloride (such as Actos, which is made by Takeda Pharmaceuticals of Lincolnshire, Ill.). The insulin is preferably an Insulin Aspart of rDNA origin (such as NovoLog, which is made by Norvo Nordisk of Princeton, N.J.). It is preferred that the cinnamon bark extract and synergistic supplement be in the form of a liquid concentrate (such as Cinnergen, which is made by NutraLab, Inc. of Cincinnati, Ohio).

Studies have shown cinnamon to be a strong potentiator of insulin [Broadhurst et al. Insulin-like Biological Activity of Culinary and Medicinal Plant Aqueous Extracts in Vitro. J.

Agric. Food Chem., 2000; 48:849-852]. One particular cinnamon extract—consisting of methyl-hydroxy-chalcone polymer (MHCP)—showed promising results in the area of glucose control. A recent study compared the effect of MHCP in 3T3-L1 adipocytes to that of insulin. [Jarvill-Taylor et al., J. Am. College Nutr., 2001; 20:327-336]. The results from that study support the theory that MHCP triggers the insulin cascade, and subsequent transport of nutrients. The study also demonstrated that MHCP treatment stimulated glucose uptake and glycogen synthesis to a similar level as insulin. The study further demonstrated that treatment with endogenous insulin and MHCP resulted in synergistic effects.

Although some have reported some level of success with an insulin and cinnamon bark extract therapy, such a therapy fails to ameliorate the diabetic symptoms for others. The present inventor is one such individual who has experimented with many different insulin therapies in an effort to control his diabetic symptoms including therapeutic formulations of cinnamon bark extract, pioglitazone, and insulin.

Such therapies were ineffective at maintaining proper carbohydrate homeostasis for the inventor. Before developing the therapeutic formulation of the present invention, the inventor's blood sugar levels ranged from 50 to 290 mg/dL with elevated hemoglobin A1c levels. Other diabetic symptoms which were not ameliorated by previous treatments include high systolic and diastolic blood pressure, weight gain, and mental cloudiness and confusion. The present inventor was able to discern a minimal level of improvement in diabetic symptoms by using cinnamon bark extract with pioglitazone hydrochloride and insulin, but the improvement was not substantial enough to warrant the added inconvenience of dosing the cinnamon bark extract. In addition, no measurable improvement was observed in blood sugar or blood pressure tests.

The inventor has developed a therapeutically effective formulation for controlling carbohydrate homeostasis which includes 1 part Insulin Aspart (NovoLog), 1 part pioglitazone hydrochloride (Actos), and 2 parts Cinnergen (all stated as parts by volume). Some variation in the mixture ratios is permissible. The following ranges provide mixture ranges, stated on the basis of a percentage of total volume:

| Ingredient | % of Total Volume |
|---|---|
| Insulin Aspart | 20-30 |
| Actos | 20-30 |
| Cinnergen | 40-60 |

Supplements as described previously may optionally be added to this mixture.

The formulation, or treatment mixture, is preferably administered in 30 cubic centimeter dosages 3 times a day. The formulation is particularly effective when administered through the urethra with a syringe. The formulation must have a viscosity such that the fluid's internal friction is low enough to be easily drawn into an injection device, such as a syringe. Absolute viscosity can be expressed in poises or centipoise (1 centipoise=0.01 poise). Biosynthetic "human" insulin varies in viscosity. Some insulin analogues have a higher viscosity while others are more fluid and have a lower viscosity. As an example, the present method is most, effective where the viscosity of the insulin aspart and the formulation is on the lower end of the known range of viscosity levels for Insulin analogs. However, the present method would not be effective if the formulation had a higher viscosity, such as 100 centipoise. Thus, a gel formulation would not be effective. A lower viscosity formulation including a low viscosity insulin aspart is lighter and therefore is delivered better and more completely to the user than a higher viscosity formulation.

The treatment mixture is applied, by depressing the syringe upward at the opening of the urethra of a male or a female. The syringe does not pierce the skin of the user, rather is released upward into the urethra opening. It is believed that this delivery method effectiveness is derived, in part, by more effectively targeting the kidneys and improving kidney operation. The transport mechanism is believed to be through the urethra into the bladder and ultimately to the pancreas. In conventional subcutaneous methods, the insulin aspart is directed to be given within 5-10 minutes of beginning a meal. Due to the present delivery method, at least in one example, the timing of the delivery is not nearly as important and the blood sugar remains stable for a longer period of time.

The abovementioned therapeutic formulation (treatment mixture) has resulted in substantially improved carbohydrate homeostasis for the inventor. Using the mentioned formulation, the inventor has experienced substantial gains in strength and endurance. Measurable improvements include reduced systolic and diastolic blood pressure (reduced from 170/94 mmHg to 125/80 mmHg), reduced weight, improved mental sharpness, improved vision, reduced hemoglobin A1c levels, and more consistent blood sugar levels with no blood sugar tests in the 50 to 85 mg/dL range. Using the previously described formulation and dosage regimen, blood sugar levels are consistently in the 89 to 200 mg/dL range. This is particularly significant since current medical research supports the link between low blood sugar episodes and heart attack events.

After 26 months on the treatment, the inventor was able to maintain suitable blood sugar levels with no medication. Thus, at least in one case, the treatment appears to have a restorative effect.

The present formulation and therapy offers other useful benefits over previous therapies. Using the present therapy, a patient has a substantially reduced risk of overdose unlike injected insulin therapies which require the injection to be administered 20 minutes prior to a meal. Also, the present therapy substantially reduces the risk of systemic and local allergic reactions. Further, it is generally not necessary to take additional blood-thinning medications or diuretics when using the present formulation.

Before beginning the previously described therapy, patients should preferably be off of the patient's previous insulin injection therapy for at least 6-10 hours. Also, patients should not switch between therapies when using the present formulation and therapy.

The preceding description contains significant detail regarding the novel aspects of the present invention. It should not be construed, however, as limiting the scope of the invention but rather as providing illustrations of the preferred embodiments of the invention. Thus, the scope of the invention should be fixed by the following claims, rather than by the examples given.

Having described my invention, I claim:
1. A method for treating diabetes in a patient, comprising:
   a. providing a treatment mixture, wherein said mixture, stated on the basis of volume, includes,
      i. between 20% and 30% insulin aspart,
      ii. between 20% and 30% pioglitazone hydrochloride,
      iii. between 40% and 60% cinnamon extract;
   b. said treatment mixture is a low-viscosity liquid between 0.1 and 1.0 centipoise;

c. loading said treatment mixture into an injecting device; and d. injecting said treatment mixture into a urethra of said patient without piercing said urethra.

2. A method for treating diabetes as recited in claim 1, wherein said injecting device is a syringe.

3. A method for treating diabetes as recited in claim 1, wherein said treatment mixture further includes a supplement selected from the group consisting of blueberry leaf extract, cranberry extract, kelp extract, sugar beet extract, acerola berry extract, ginger root extract, black cherry extract, green tea extract, Irish moss extract, *aloe vera* extract, and Stevia leaf extract.

4. A method for treating diabetes in a patient, comprising
a. providing a treatment mixture, wherein said mixture, stated on the basis of volume, includes,
   i. between 20% and 30% insulin aspart,
   ii. between 20% and 30% pioglitazone hydrochloride,
   iii. between 40% and 60% cinnamon extract;
b. said insulin aspart having a viscosity lower than 90 centipoise and said treatment mixture is a low-viscosity liquid between 0.1 and 1.0 centipoise;
c. loading said treatment mixture into an injecting device; and
d. injecting said treatment mixture upward into a urethra of said patient without piercing said urethra.

5. A method of treating diabetes as recited in claim 4, wherein injecting device is a syringe.

6. A method for treating diabetes as recited in claim 4, wherein said insulin aspart has a viscosity between 0.1 centipoise and 10 centipoise.

7. A method for treating diabetes as recited in claim 5, wherein said treatment mixture has a viscosity such that said treatment mixture can be easily drawn up into said syringe and released effectively upward into said urethra of said patient.

8. A method of treating diabetes as recited in claim 7, wherein said treatment mixture is capable of vaporizing within said urethra of said patient.

9. A method of treating diabetes as recited in claim 6, wherein said treatment mixture is released upward into an opening of said urethra.

10. A method of treating diabetes as recited in claim 7, wherein said treatment mixture can be administered at any set time during a day.

* * * * *